(12) United States Patent
Wang et al.

(10) Patent No.: US 12,259,330 B2
(45) Date of Patent: Mar. 25, 2025

(54) CHARGE-SENSITIVE OPTICAL DETECTION OF BINDING KINETICS BETWEEN PHAGE DISPLAYED PEPTIDE LIGANDS AND PROTEIN TARGETS

(71) Applicant: ARIZONA BOARD OF REGENTS ON BEHALF OF ARIZONA STATE UNIVERSITY, Scottsdale, AZ (US)

(72) Inventors: Shaopeng Wang, Chandler, AZ (US); Runli Liang, Mesa, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 18/689,180

(22) PCT Filed: Aug. 26, 2022

(86) PCT No.: PCT/US2022/075532
§ 371 (c)(1),
(2) Date: Mar. 5, 2024

(87) PCT Pub. No.: WO2023/039342
PCT Pub. Date: Mar. 16, 2023

(65) Prior Publication Data
US 2024/0272082 A1   Aug. 15, 2024

Related U.S. Application Data

(60) Provisional application No. 63/261,005, filed on Sep. 8, 2021.

(51) Int. Cl.
*G01N 21/77* (2006.01)
*G01N 27/30* (2006.01)
*G01N 33/543* (2006.01)

(52) U.S. Cl.
CPC ....... *G01N 21/7703* (2013.01); *G01N 27/305* (2013.01); *G01N 33/5438* (2013.01)

(58) Field of Classification Search
None
See application file for complete search history.

(56) References Cited

U.S. PATENT DOCUMENTS 7,900,527 B1 * 3/2011 Su .......................... G02B 6/107
73/866.1
2004/0005540 A1 * 1/2004 Petrenko .............. G01N 33/569
435/5

(Continued)

FOREIGN PATENT DOCUMENTS

KR      20180097347 A  *  8/2018  ....... G02B 6/020242

OTHER PUBLICATIONS

Guan et al. "Detection of molecular binding via charge-induced mechanical response of optical fibers." Chem. Sci., 2014, 5, 4375-4381. (Year: 2014).*

(Continued)

*Primary Examiner* — William H. Beisner
(74) *Attorney, Agent, or Firm* — MH2 Technology Law Group LLP

(57) ABSTRACT

Provided herein are systems for the label-free detection of target molecules in samples. The systems include a sensor probe positioned in a sensing region and configured to bind to receptors for the target molecules. The systems also include electrodes configured to expose the sensor probe to an alternating electric field, and a light source optically coupled to the sensor probe and configured to provide light along a length of the sensor probe. In addition, the systems also include a position sensitive photodetector configured to detect a position of light exiting the sensor probe, and a processor configured to assess, based at least in part on the position of the light exiting the sensor probe, an amplitude (Continued)

of oscillation of the sensor at a frequency of the alternating electric field and a direction of a displacement of the sensor. Additional systems and related methods are also provided.

23 Claims, 7 Drawing Sheets

(56) References Cited

U.S. PATENT DOCUMENTS

| | | |
|---|---|---|
| 2005/0129073 A1 | 6/2005 | Nguyen et al. |
| 2006/0148100 A1* | 7/2006 | Madison ............ G01N 33/6878 |
| | | 436/518 |
| 2008/0154128 A1 | 6/2008 | Milner |
| 2010/0044211 A1 | 2/2010 | Kwon et al. |
| 2012/0234393 A1 | 9/2012 | Maltezos et al. |
| 2018/0156752 A1* | 6/2018 | Tao ........................ G01N 27/60 |

OTHER PUBLICATIONS

Knez et al. "Affinity Comparison of p3 and p8 Peptide Displaying Bacteriophages Using Surface Plasmon Resonance." Anal. Chem. 2013, 85, 10075-10082. (Year: 2013).*

Zhang et al. "Label-free aptamer-based detection of microcystin-LR using amicrocantilever array biosensor." Sensors and Actuators B 260 (2018) 42-47. (Year: 2018).*

Murugan et al., P-Fab: A Fiber-Optic Biosensor Device for Rapid Detection of COVID-19, Transactions of the Indian National Academy of Engineering, 2020, 5, pp. 211-215.

International Search Report and Written Opinion dated Jan. 29, 2023, PCT Application No. PCT/US2022/075532, 11 pages.

* cited by examiner

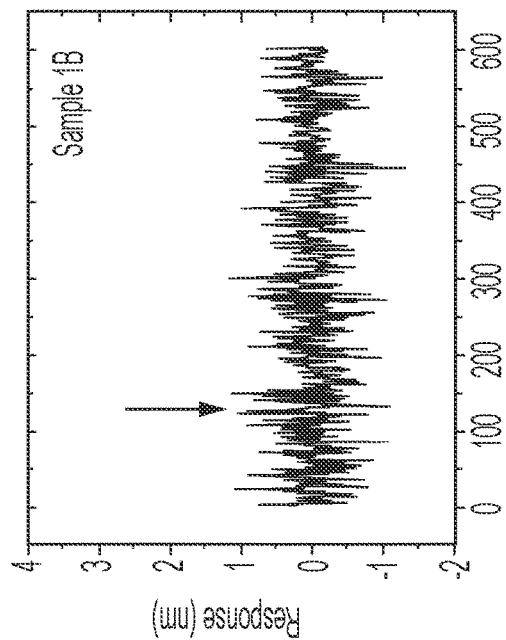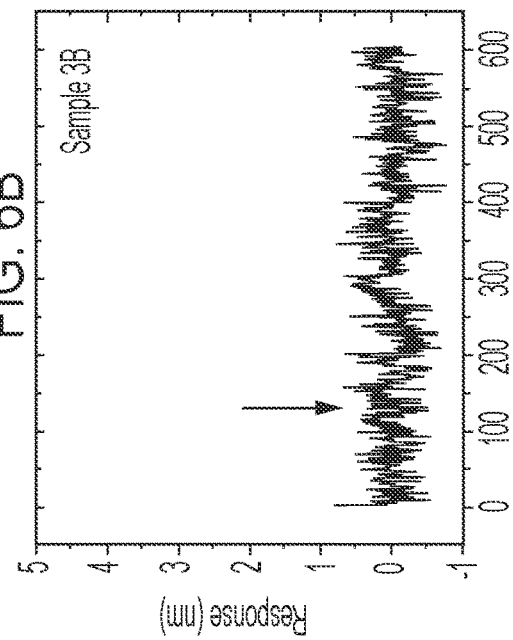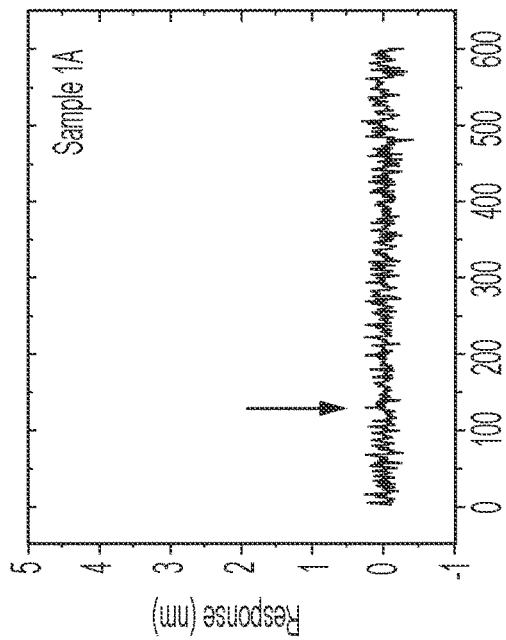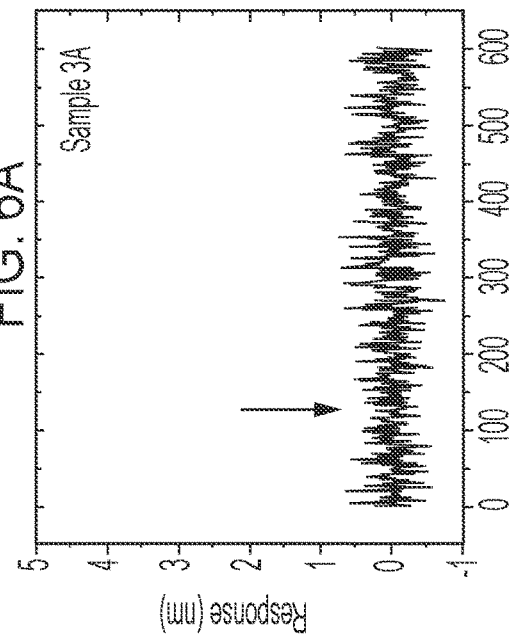

CHARGE-SENSITIVE OPTICAL DETECTION OF BINDING KINETICS BETWEEN PHAGE DISPLAYED PEPTIDE LIGANDS AND PROTEIN TARGETS

CROSS-REFERENCE TO RELATED APPLICATIONS

This application is the national stage entry of International Patent Application No. PCT/US2022/075532, filed on Aug. 26, 2022, and published as WO 2023/039342 A1 on Mar. 16, 2023, which claims the benefit of U.S. Provisional Patent Application Ser. No. 63/261,005, filed Sep. 8, 2021, the disclosure of which is hereby incorporated by reference herein in its entirety.

STATEMENT REGARDING FEDERALLY SPONSORED RESEARCH OR DEVELOPMENT

This invention was made with government support under grants R33CA202834 and R44GM139535 awarded by the National Institutes of Health. The government has certain rights in the invention.

TECHNICAL FIELD

This invention relates to charge-sensitive detection systems and methods for direct quantification of binding kinetics of phage displayed peptides.

BACKGROUND

The global peptide therapeutics market is one of the fastest growing segments of the pharmaceutical industry right now, with the market valued at USD 20 billion in 2017 and expected to gain USD 50 billion in revenues by 2024. Compared to small molecule drugs, peptides have greater efficacy, selectivity, and specificity, with lower risks of systemic toxicity and complications. Compared to other biological drug candidates, such as antibodies and proteins, peptides are cheaper to manufacture and are smaller in molecule size so that it is easier for peptides to penetrate into organs or tumors. Peptides also offer higher activity per unit mass with greater stability compared to other biological drugs. Phage display technology is one of the most widely used in vitro display technologies that offers high transformation efficiency with unique peptide clones. In addition, a higher number of copies can be displayed with phage than in other in vitro display technologies.

One bottleneck in phage display technology is the triage of hundreds of lead molecules for follow-up characterization. Currently, ELISA is the only commonly used method for triaging clones while the displayed peptides are still on the phage's surface. However, many peptides are displayed in multivalent form; thus, the ELISA signal reflects a combination of valency and affinity. Recent studies have found that multivalency and the spatial configuration of binding sites can significantly influence binding kinetics. In this case, only qualitative data are provided. To find the best drug candidates from hundreds of positive peptides screened out of a phage-displayed peptide library, binding kinetics data between the peptide and the target protein is needed. In current practice, candidate peptides need to be custom synthesized for their binding kinetics measurement, and the process is costly and time-consuming.

It can be challenging to use conventional label-free detection methods to measure phage-displayed peptide binding kinetics directly, such as surface plasmon resonance (SPR) or bio-layer interferometry (BLI). SPR has been used to determine the affinity of phage-displayed peptides; however, direct measurements of binding kinetics of the peptides displayed on the phage often proves to be difficult due to the following reasons: (1) the huge mass of phage shifting the baseline out of detection range when the phage is loaded onto the sensor's surface, (2) the surface density of the displayed peptides being limited by the expression level and the huge mass ratio between the phage and the peptide, and (3) the multivalent nature of phage-expressed peptides making the sensor response curves reflect the collective effect of multivalency binding kinetics instead of one-to-one first-order binding kinetics if loading the target protein onto the sensor's surface. While electrochemical detection methods have been used in phage display technology, they focus on studying the capture of *E. coli* or other bacterial cells using phages. Thus, it is still challenging to measure the binding kinetics of phage-displayed peptides or antibodies without the synthesis or purification of the peptides or antibodies.

Accordingly, there is a need for additional methods, and related aspects, for detecting the binding kinetics between phage-displayed peptide ligands and target molecules, such as peptides and proteins.

SUMMARY

This disclosure describes methods and systems for combining charge-sensitive optical detection (CSOD) with phage display technology to enable rapid quantification of peptide binding kinetics directly on the whole phage. These methods and systems obviate the need to synthesize pure peptides and proteins required by other approaches, thereby saving time and improving the precision and accuracy of the selection. Moreover, the CSOD methods of the present disclosure typically measure molecular interaction kinetics by detecting the binding-induced charge changes, which can overcome the mass sensitivity limit. This unique feature provides CSOD with higher sensitivity than conventional mass sensitive label-free methods in measuring phage-target binding kinetics. These and other attributes will be apparent upon complete review of the present disclosure.

In one aspect, the present disclosure provides a system for detecting target molecules in a sample. The system includes a sample well defining a sensing region and two electrode regions, a sensor probe positioned in the sensing region and configured to bind to receptors for target molecules, and an electrode positioned in each electrode region and configured to expose the sensor probe to an alternating electric field, wherein the sensing region defines a channel between the electrodes. The system also includes a light source optically coupled to the sensor probe and configured to provide light along a length of the sensor probe, a position sensitive photodetector configured to detect a position of light exiting the sensor probe, and a processor configured to assess, based at least in part on the position of the light exiting the sensor probe, an amplitude of oscillation of the sensor at a frequency of the alternating electric field and a direction of a displacement of the sensor. The receptors comprise phages or phages displaying peptides, proteins, or antibodies, and the target molecules comprise peptides, proteins, or both.

Various optional features of the above embodiments include the following. The sensor probe is an optical fiber. A diameter of the optical fiber is in a range of about 100 μm to about 1000 μm. A resonance frequency of the optical fiber is in a range of about 100 Hz to about 20 kHz. The optical fiber is etched with a strong acid (e.g., hydrofluoric acid or the like) for less than 1 minute. The optical fiber is not etched with a strong acid. The position sensitive detector is a quadrant cell photodetector. A bandwidth of the quadrant cell photodetector is about 150 kHz. The frequency of the alternating electric field is in a range of about 5 Hz to about 20 kHz. The phages are whole phages. The light source comprises a laser, a light emitting diode, or a lamp. The receptors and target molecules are label-free.

In another aspect, the present disclosure provides a system for detecting target molecules in a sample. The system includes a sample container comprising two electrode regions and a sensing region disposed between the electrode regions, and an optical fiber positioned or positionable in the sensing region, which optical fiber comprises phage-displayed peptide ligands that bind the target molecules in the sample. The system also includes an electrode positioned or positionable in each electrode region and configured to expose the optical fiber to an alternating electric field, a light source optically coupled to the optical fiber and configured to provide light along a length of the optical fiber, and a position sensitive photodetector (e.g., a quadrant cell photodetector, a bi-cell photo detector, a linear array photo detector, or any other type of position sensitive photodetectors) configured to detect a position of light exiting the optical fiber.

Various optional features of the above embodiments include the following. The system further comprises a processor operably coupled at least to the position sensitive photodetector, which processor is configured to assess, based at least in part on the position of the light exiting the optical fiber, an amplitude of oscillation of the optical fiber at a frequency of the alternating electric field and a direction of a displacement of the optical fiber. The target molecules comprise peptides, proteins, or both. The phage-displayed peptide ligands comprise peptides, proteins, or antibodies. The phage-displayed peptide ligands and target molecules are label-free. A diameter of the optical fiber is in a range of about 100 μm to about 1000 μm. A resonance frequency of the optical fiber is in a range of about 100 Hz to about 20 kHz. A bandwidth of the quadrant cell photodetector is about 150 kHz. The frequency of the alternating electric field is in a range of about 5 Hz to about 20 kHz. The light source comprises a laser, a light emitting diode, or a lamp. The sample container comprises a microplate having a plurality of wells and wherein the optical fiber and the electrodes are positionable in one or more of the plurality of wells such that when the optical fiber and the electrodes are positioned in a given well of the microplate, the given well comprises the electrode and sensing regions.

In yet another aspect, the present disclosure provides a method of analyzing a solution to assess the presence target molecules in a sample. The method includes providing the sample to a sensing region of a sample well, contacting the sample with a sensor probe comprising molecular receptors configured to interact with the target molecules, and providing light along a length of the sensor probe. The method also includes applying an alternating electric field perpendicular to the length of the sensor probe, detecting a position of light exiting the sensor probe, and assessing, based at least in part on the position of light exiting the sensor probe, an amplitude of the oscillation of the sensor probe. In addition, the method also includes assessing, based at least in part on the amplitude of the oscillation of the sensor probe, the binding kinetics of the target molecules, wherein the molecular receptors comprise phages or phages displaying ligands, and the target molecules comprise peptides, proteins, or both.

In yet another aspect, the present disclosure provides a method of analyzing a solution to assess the presence target molecules in a sample. The method includes contacting the sample with a sensor probe that comprises phage-displayed peptide ligands that bind the target molecules in the sample, applying an alternating electric field perpendicular to the length of the sensor probe, and detecting a position of light exiting the sensor probe (e.g., using a position sensitive photodetector, such as a quadrant cell photodetector or the like). The method also includes assessing, based at least in part on the position of light exiting the sensor probe, an amplitude of the oscillation of the sensor probe, and assessing, based at least in part on the amplitude of the oscillation of the sensor probe, the binding kinetics of the target molecules.

Various optional features of the above embodiments include the following. The phages comprise whole phages. The target molecules are electrically charged. The method further includes binding the target molecules to the molecular receptors. The sensor probe comprises an optical fiber. An amplitude of the oscillation of the optical fiber is in a range of 1 nm to 10,000 nm. A frequency of the oscillation of the optical fiber is in a range of 5 Hz to 20 kHz. The assessing the amplitude of the oscillation of the optical fiber comprises detecting the oscillation with a position sensitive photodetector. The position sensitive photodetector is a quadrant cell photodetector.

The details of one or more embodiments of the subject matter of this disclosure are set forth in the accompanying drawings and the description. Other features, aspects, and advantages of the subject matter will become apparent from the description, the drawings, and the claims.

BRIEF DESCRIPTION OF DRAWINGS

FIGS. 6A-6D show CSOD measurement results of PCSK9 binding to negative samples. Sample IDs are labeled on the top right corner of each plot. The arrows indicate switching the fiber probe from the buffer well to a well with 1000 nM PCSK9 solution.

DEFINITIONS

Figure 1:
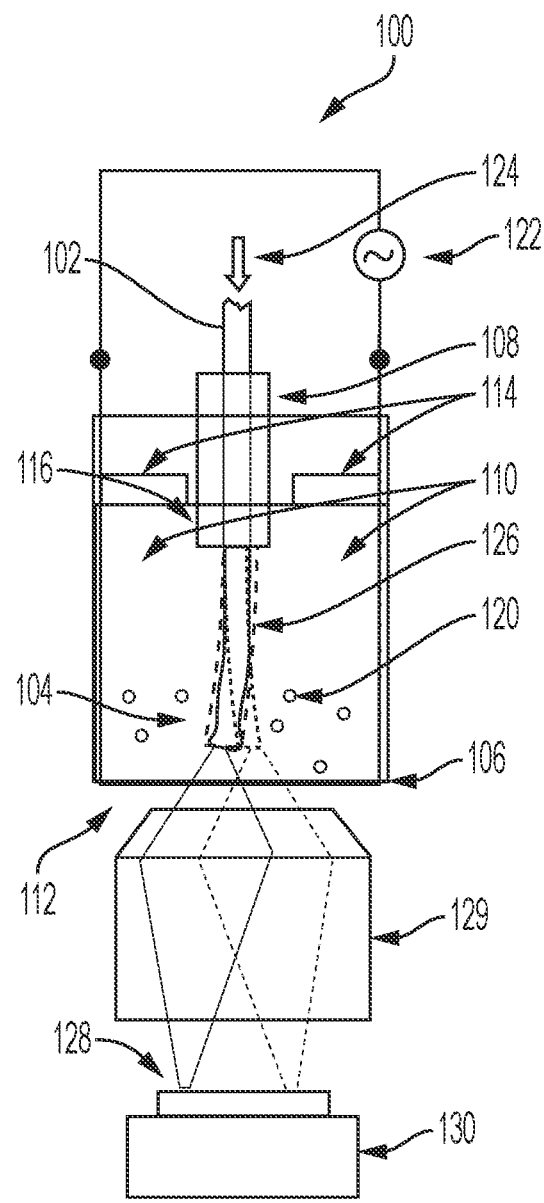
FIG. 1 is a schematic side cutaway view of a charge-sensitive optical detection (CSOD) system according to an exemplary embodiment.

In order for the present disclosure to be more readily understood, certain terms are first defined below. Additional definitions for the following terms and other terms may be set forth throughout the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, systems, and computer readable media, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Antibody: As used herein, the term "antibody" refers to an immunoglobulin or an antigen-binding domain thereof. The term includes but is not limited to polyclonal, monoclonal, monospecific, polyspecific, non-specific, humanized, human, canonized, canine, felinized, feline, single-chain, chimeric, synthetic, recombinant, hybrid, mutated, grafted, and in vitro generated antibodies. The antibody can include a constant region, or a portion thereof, such as the kappa, lambda, alpha, gamma, delta, epsilon and mu constant region genes. For example, heavy chain constant regions of the various isotypes can be used, including: IgG1, IgG2, IgG3, IgG4, IgM, IgA1, IgA2, IgD, and IgE. By way of example, the light chain constant region can be kappa or lambda. The term "monoclonal antibody" refers to an antibody that displays a single binding specificity and affinity for a particular target, e.g., epitope.

Binding Affinity: As used herein, the term "binding affinity", typically refers to a strength of non-covalent association between or among two or more entities.

Ligand: As used herein, "ligand" refers to a substance that forms a complex with another molecule, such as a biomolecule.

Peptide: As used herein, "peptide" refers to a sequence of 2-50 amino acids attached one to another by a peptide bond. These peptides may or may not be fragments of full proteins.

Phage-Displayed Peptide Ligand: As used herein, "phage-displayed peptide ligand" refers to a ligand of interest, such as a peptide or protein that is presented or "displayed" on the surface of a bacteriophage. Typically, one or more genes encoding a peptide or protein of interest are inserted into the bacteriophage, causing the phage to "display" the peptide or protein on its surface upon expression.

Protein: As used herein, "protein" or "polypeptide" refers to a polymer of typically more than 50 amino acids attached to one another by a peptide bond. Examples of proteins include enzymes, hormones, antibodies, peptides, and fragments thereof.

System: As used herein, "system" in the context of analytical instrumentation refers a group of objects and/or devices that form a network for performing a desired objective.

DETAILED DESCRIPTION

To find the best drug candidates out of hundreds of positive peptides screened out of a phage displayed peptide library, binding kinetics data between the peptide and the target protein are typically needed. However, direct measurement of binding kinetics by label-free detection methods (e.g., surface plasmon resonance and bio-layer interferometry) of peptides displayed on the phage can be difficult for several reasons. First, the large molecular mass of the phage makes the loading of phage onto the sensor shifts the baseline of detection range. Second, the surface density of the displayed peptides is limited by the expression level and the large mass ratio between the phage and the peptide. Third, the multivalent nature of phage expressed peptides can make the sensor response curve reflect the collective effect of multi-valency binding kinetics instead of one-to-one first order binding kinetics.

This disclosure describes methods and systems that combine charge-sensitive optical detection (CSOD) with phage display technology to enable rapid quantification of peptide binding kinetics directly on the whole phage. These and other attributes will be apparent upon a complete review of the present disclosure, including the accompanying figures.

To illustrate, FIG. 1 is a side cutaway view of a charge sensitive optical detection (CSOD) system 100. A sensor (e.g., a filament or optical fiber) 102 functionalized with phage-displayed peptide ligands 104 is positioned in a sample well 106. The optical fiber 102 is typically a glass optical fiber. The optical fiber 102 may be stabilized, for example, with tube 108. Sample well 106 includes solution 110 between electrode regions 112 including electrodes 114. Sensing region 116 is defined by a space in the solution 110 between electrodes 114. Optical fiber 102 is positioned in sensing region 116 such that phage-displayed peptide ligands 104 on the optical fiber are positioned in sensing region 116. In some embodiments, if a target molecule (e.g., peptide or protein) 120 in the solution 110 contains electrically charged moiety, binding of the target molecule to the phage-displayed peptide ligands 104 changes the surface charge of the optical fiber 102. In some embodiments, phage-displayed peptide ligands 104 can be selected to interact with primary amine groups in the target molecules (e.g., proteins or peptides).

To monitor the change in charge, an alternating electric field from source 122 is applied perpendicular to the optical fiber 102 and drives the optical fiber to oscillate. The oscillation amplitude is proportional to the surface charge of the optical fiber 102. The electrodes 114 are configured to expose the sensor to the alternating electric field. Thus, CSOD can be used to precisely measure the oscillation amplitude.

To measure the oscillation amplitude, light 124 is coupled into the optical fiber 102, and the oscillation of the fiber tip 126 is tracked from the optical image 128 of the fiber tip, together with a differential optical position tracking algorithm. The optical image 128 of the tip can be magnified (e.g., with an objective 129) and captured with a detector 130. Detector 130 may be an optical imager or a position sensitive photodetector (e.g., a quadrant cell photodetector or the like).

To further illustrate, a CSOD system of the present disclosure typically includes a glass optical fiber tip functionalized with peptide displayed phages that is dipped into a microplate well or another sample container. In some embodiments, the diameter of the optical fiber is in a range of about 100 μm to about 1000 μm), and the tip of the optical fiber is in a range of about 5 mm to about 50 mm. If the solution well contains molecular ligands with charge or charged functional groups, binding of the ligands to the phage changes the net charge on the fiber surface. To monitor the charge change, an alternating electric field is applied perpendicular to the optical fiber and drives the fiber to oscillate. The oscillation amplitude is proportional to the surface charge of the optical fiber. To measure the oscillation amplitude, light is coupled into the fiber, and the oscillation of the fiber is tracked using a position sensitive photodetector (e.g., a quadrant cell photodetector). In some embodiments, the output of the detector is converted to oscillation amplitude by fast Fourier transform (FFT) processing of the differential signal.

In some embodiments, the systems of the disclosure include position sensitive photodetectors, such as quadrant cell photodetectors. A quadrant cell photo detector provides a high bandwidth (up to about 150 kHz) and allows detection at a high fiber oscillation frequency up to about 75 kHz. Together, the high bandwidth and high detection frequency make it possible to use a larger diameter optical fiber rather than a smaller diameter optical fiber (e.g., about 15 μm to about 50 μm in diameter) that can be required for other detectors, such as charge coupled detector (CCD) video cameras. In addition, the larger diameter fiber has a higher resonance frequency (100 Hz to 20 kHz) than the smaller diameter fiber (5 Hz to 80 Hz), thereby reducing interference from environmental noise. The larger fiber is also mechanically more stable, with less low frequency drift than the small diameter fiber. In addition, preparing the larger diameter fiber can be done by stripping the fiber coating and can require little or no etching. When the larger diameter fiber is etched, a duration of the etching can be as short as 30 seconds, compared to the 30 minutes typically needed for the smaller diameter. Thus, use of the larger diameter fiber can reduce or eliminate the use of toxic chemicals needed for etching, such as concentrated hydrofluoric acid. Use of the larger diameter fiber also simplifies the fabrication process, making it simpler and safer as well as quicker. The principle of CSOD has been described in detail previously in, for example, U.S. Pat. No. 9,772,305 and US Pat. Pub. No. 2022/0018808, which are both incorporated by reference.

Figure 2:
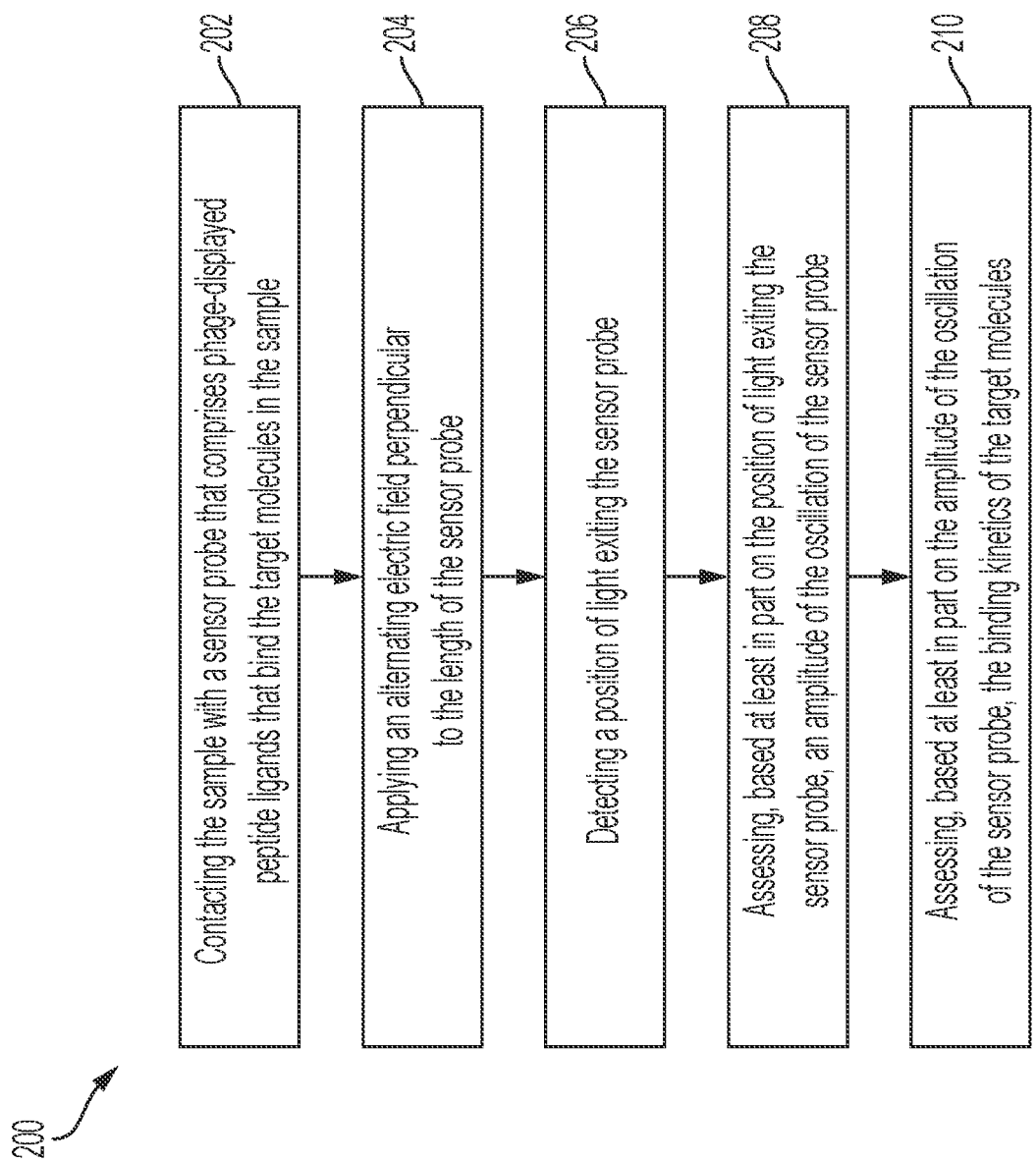
FIG. 2 is a flow chart that schematically shows exemplary method steps of analyzing a solution to assess the presence target molecules in a sample according to some aspects disclosed herein.

FIG. 2 is a flow chart that schematically shows exemplary method steps of analyzing a solution to assess the presence target molecules in a sample according to some aspects disclosed herein. As shown, method 200 includes contacting the sample with a sensor probe that comprises phage-displayed peptide ligands that bind the target molecules in the sample (step 202) and applying an alternating electric field perpendicular to the length of the sensor probe (step 204). Method 200 also includes detecting a position of light exiting the sensor probe (step 206) and assessing, based at least in part on the position of light exiting the sensor probe, an amplitude of the oscillation of the sensor probe (step 208). In addition, method 200 also includes assessing, based at least in part on the amplitude of the oscillation of the sensor probe, the binding kinetics of the target molecules (step 210).

In some embodiments of the CSOD workflows of the present disclosure, light exiting out of a fiber tip is projected on the center of a quadrant cell detector. In some embodiments, sensor response is calculated with the equation:

$$\text{Response} = \frac{(Q1 + Q3) - (Q2 + Q4)}{(Q1 + Q3) + (Q2 + Q4)}$$

where Q1 to Q4 are the signals collected by the quadrant cell detector. In some embodiments, phages used in the methods disclosed herein comprise whole phages. In some embodiments, the target molecules (peptides, proteins, etc.) are electrically charged. The methods typically further include binding the target molecules to the molecular receptors (e.g., phage-displayed antibodies or other peptide ligands). In some embodiments, the sensor probe comprises an optical fiber. In some embodiments, an amplitude of the oscillation of the optical fiber is in a range of 1 nm to 10,000 nm. In some embodiments, a frequency of the oscillation of the optical fiber is in a range of 5 Hz to 20 kHz. In some embodiments, the amplitude of the oscillation of the optical fiber is assessed by detecting the oscillation with a position sensitive photodetector. In some embodiments, the position sensitive photodetector is a quadrant cell photodetector.

Figure 3:
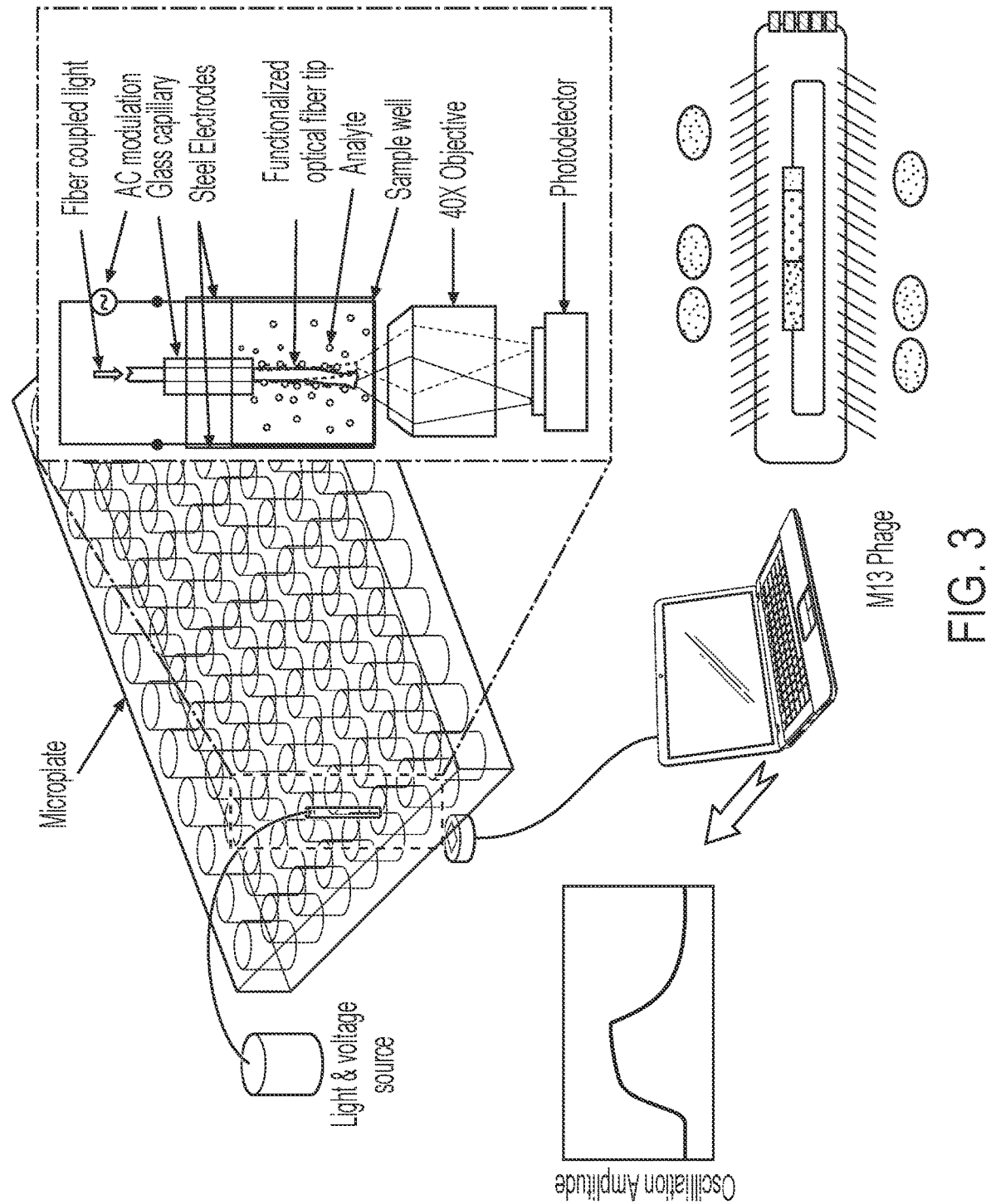
FIG. 3 is a schematic of charge-sensitive optical detection of binding kinetics between M13 phage-displayed peptides and the protein target. An optical fiber is inserted into a glass capillary and the fiber tip is dipped into a microplate well between a pair of steel electrodes. An alternating electric field is applied through the electrodes to drive the fiber tip into oscillation. The light coming out from the tip bottom is collected by a 40× objective and measured by a quadrant cell detector. For the binding kinetics measurement, the M13 phages with peptides displayed on pVIII coating proteins are immobilized on the fiber tip, and the tip is inserted into a well with target protein. Upon binding, the net charges of the M13 phages are changed and the oscillation amplitude of the fiber tip changes as well. By recording the oscillation change in real-time, the binding kinetics between the peptide, and the protein can be quantified.

Example: Charge-Sensitive Optical Detection of Binding Kinetics Between Phage-Displayed Peptide Ligands and Protein Targets Detection Principle A schematic of the CSOD system is shown in FIG. 3. The principle of CSOD has been described in detail previously in, for example, U.S. Pat. No. 9,772,305 and US Pat. Pub. No. 2022/0018808, which are both incorporated by reference. Briefly, a stripped glass optical fiber with a tip (length ~10 mm) functionalized with protein samples is dipped into a microplate well. If the solution well contains molecular ligands with charge or charged functional groups, the binding of the ligands to the proteins changes the net charge on the fiber's surface. To monitor the charge change, an alternating electric field is applied perpendicular to the optical fiber and drives the fiber for oscillation. The oscillation amplitude is proportional to the surface charge of the optical fiber. The fiber oscillation amplitude is related to electric field strength, frequency, surface charge density, and fiber dimensions (length and diameter). The relationship is given by the following:

$$x = \frac{2\pi |\vec{E(\omega)}| \sigma r l}{\sqrt{(k_{eff} - m_{eff}\omega^2)^2 + (c\omega)^2}} \quad (1)$$

where $|\vec{E(\omega)}|$ is the electric field strength applied to the fiber, c is the damping coefficient, and keff, meff, r, and l are the effective spring constant, mass, radius, and length of the optical fiber, respectively. The effective spring constant, keff, of the cylindrical optical fiber is given by the following:

$$k_{eff} = \frac{3\pi E r^4}{4 l^3} \quad (2)$$

where E is the Young's modulus. The electric field applied is frequency dependent and is given by the following:

$$|\vec{E(\omega)}| = |\vec{E_0}| \frac{R_S}{\sqrt{R_S^2 + \frac{1}{(\omega C_{eff})^2}}} \quad (3)$$

where $|\vec{E_0}|$ is the input electric field between the electrodes, and Rs and Ceff are the solution resistance and effective interfacial capacitance of electrode/solution interface, respectively. Equations (1)-(3) show that the oscillation amplitude is both frequency and fiber dimension-dependent. In our previous studies, we typically use fibers with a small diameter (around 15 μm), and the optimal frequency where fiber oscillates at maximum amplitude is usually low (below 60 Hz), which is suitable for detections with a CCD camera with a limited frame rate. Since CSOD detects the mechanical motion of the fiber tip, the oscillation signal is sensitive to environmental mechanical noise. From a noise spectrum analysis where no electric field was added, the noise levels are much higher in the low frequency region, which are mostly from environmental and system mechanical noises that are hard to isolate at low frequencies. In this study, we used larger diameter fibers (around 120 μm) with higher resonance frequency and achieved four times improved signal-to-noise ratio. Using large fiber also significantly reduced the usage time of the toxic hydrofluoric acid for fiber etching from ~30 min to ~30 s, with the possibility to eliminate this step. For sustained recordings of the high frequency signal, we replaced the CCD camera with a high-speed photo detector, which reduced the data size by three orders of magnitude due to the photodetector recording only differential and sum signals, rather than the image stacks recorded by the camera. These implementations dramatically improved the performance of CSOD technology and prepared it for future developments of high-throughput detection. Additional detail regarding this example are provided in Liang et al., Charge-Sensitive Optical Detection of Binding Kinetics between Phage-Displayed Peptide Ligands and Protein Targets. Biosensors 2022, 12, 394, which is incorporated by reference, including all supplemental information disclosed therein.

Figure 4A:
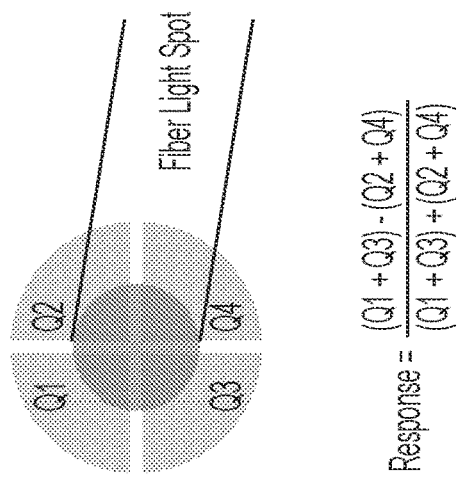
FIGS. 4A-4E show an example of charge-sensitive optical detection workflow. (a) Schematic shows the light out of the fiber tip projected on the center of the quadrant cell detector, where the sensor response is calculated with the equation shown on the right. Q1 to Q4 are the signals collected by the quadrant cell detector. (b) Representative measured detector response plotted against time with a sampling rate of 16.000 data points per second. (c) The calibration curve and linear region of the quadrant cell detector. (d) The calibrated fiber oscillation amplitudes over time. (e) The fast Fourier transform (FFT) result of the fiber oscillation amplitude in 1 s, where the peak at 511 Hz clearly shows the fiber vibrates at the set frequency.
Figure 4B:
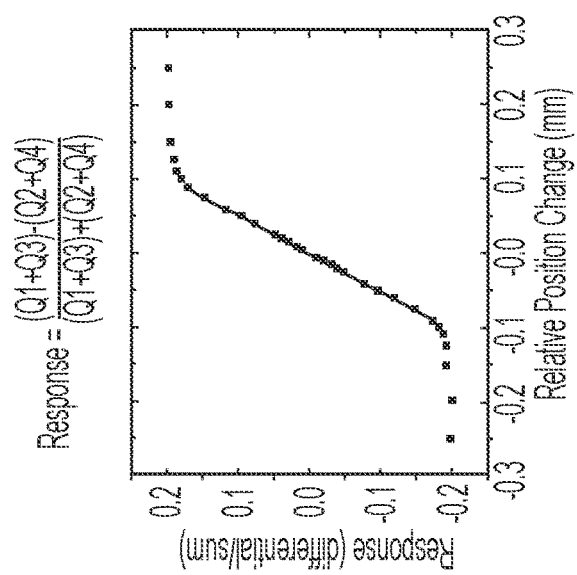
Figure 4C:
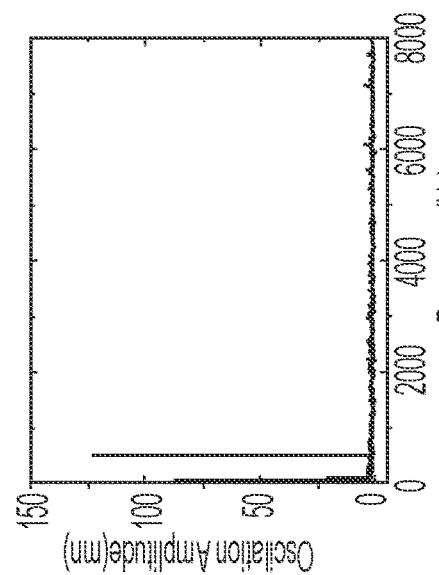
Figure 4D:
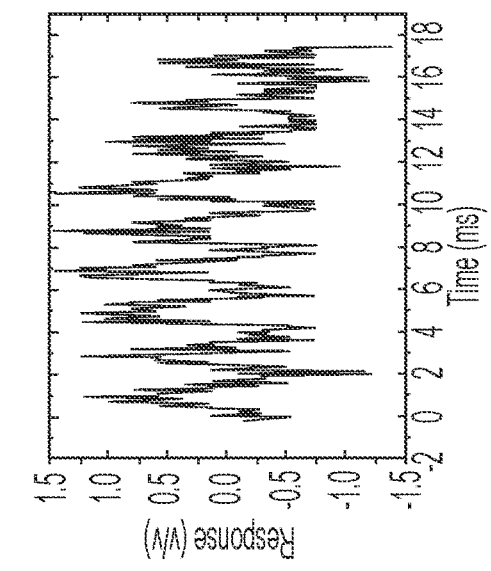
Figure 4E:
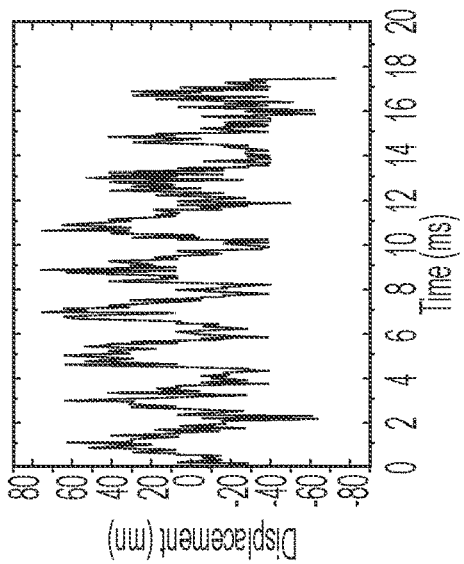
Figure 5A:
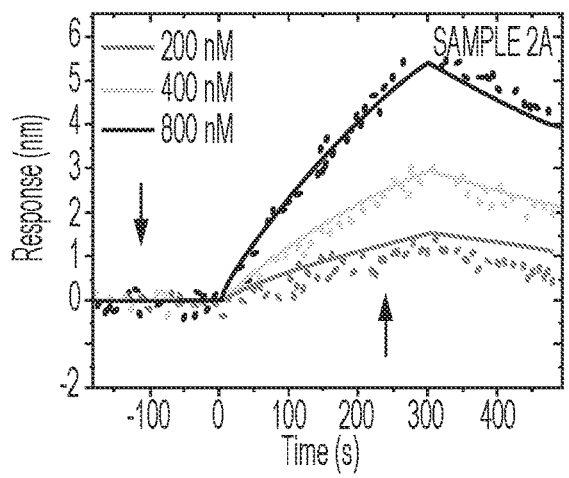
FIGS. 5A-5F show CSOD measurement results of PCSK9 binding to different peptides displayed on M13 phage surface. Sample IDs are marked on the top right corner of each plot, and the details of the samples are listed in Table 2. Binding curves for different peptides. The fiber probes were switched from a well containing a buffer to a well containing PCSK9 at 0 s for the measurement of the association process (downward facing arrow) and then switched back to the buffer well at the time indicated by the upward facing arrow for the measurement of the dissociation process.
Figure 5B:
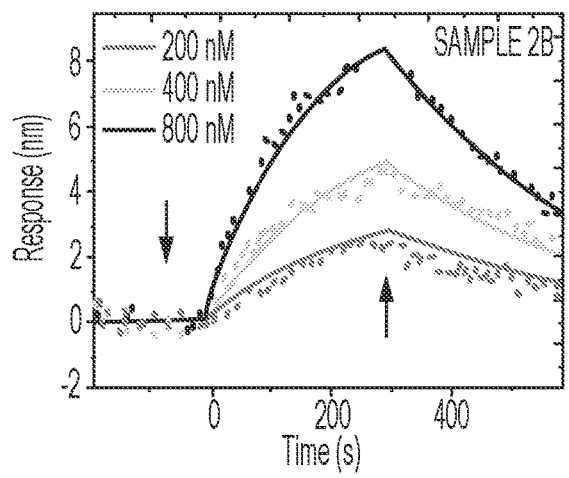
Figure 5C:
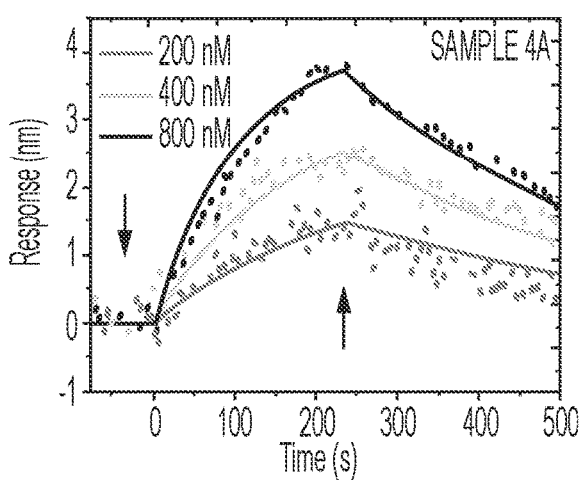
Figure 5D:
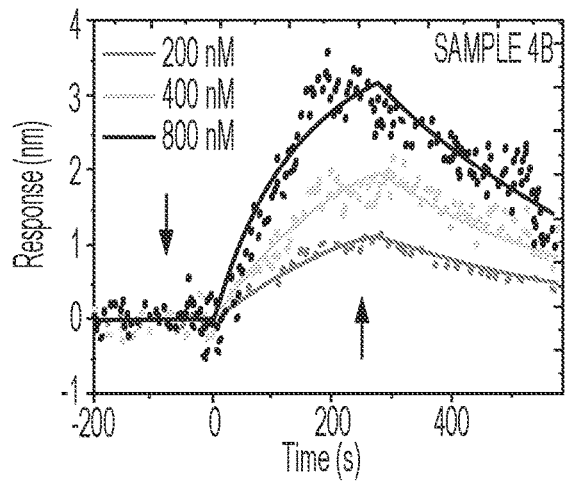
Figure 5E:
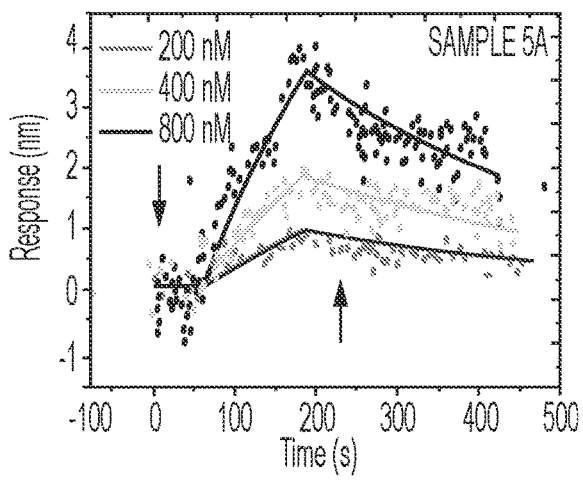
Figure 5F:
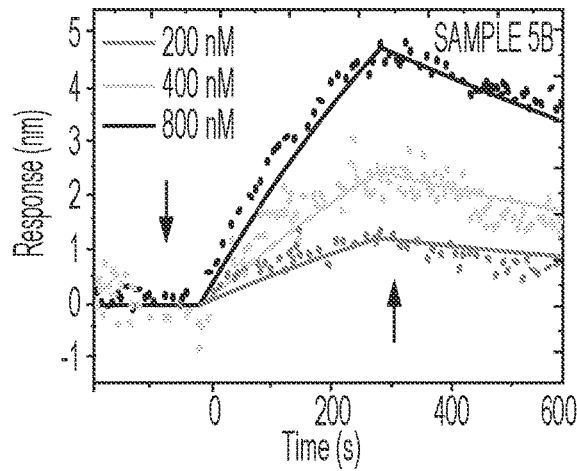

To measure the oscillation amplitude, light is coupled into the fiber and received by a quadra-cell position-sensitive photodetector placed under the fiber tip (FIG. 3). The oscillation of the fiber changes the position of the outcoming light spot on the detector and is recorded in real-time using a differential algorithm (FIG. 4a). The electric output of the detector (FIG. 4b) is then converted to the relative position change in nanometers using a calibration curve (FIG. 4c, see also Methods), and the oscillation profile of the fiber tip can be obtained (FIG. 4d). Fast Fourier transform (FFT) is applied to the oscillation profile every one second. The FFT spectrum shows a pronounced peak at 511 Hz, which is the frequency being applied, and the height of the peak represents the oscillation amplitude of the fiber tip (FIG. 4e).

Materials and Methods

Materials

Multimode optical fibers (125 μm in diameter, FG105UCA, Thorlabs, Newton, NJ, USA) were purchased from Thorlabs, Inc. Phosphate-buffered saline (PBS) was purchased from Mediatech Inc., Manassas, VA, USA. The drug target proprotein convertase subtilisin/kexin type 9 (PCSK9) was provided by Dr. Daniel Kirchhofer at Genentech. N-hydroxysulfosuccinimide (NHS), N-(3-dimethylaminopropyl)-NO-ethylcarbodiimide hydrochloride (EDC), and O-(2-carboxyethyl)-O'-(2-mercaptoethyl) heptaethylene glycol (SH-PEG8-COOH) were purchased from Sigma-Aldrich. Streptavidin, methyl-PEG4-thiol (MT(PEG)4) and SuperBlock blocking buffer were purchased from Thermo Fisher Scientific. Deionized (DI) water with a resistivity of 18.2 MΩ cm filtered through a 0.45 μm filter was used in all experiments. Other chemicals were purchased from Sigma-Aldrich.

Generation of M13 Phage Displayed Peptides

Five different M13 phage samples were generated and used as listed in Table 1. The peptides were fused to the N-terminus of M13 major coat protein (pVIII) utilizing two different types of secretion signal peptides (Table 1), with or without the leading sequence of Ser-Gly (SG) extension at the N-terminus of the peptide. Peptides with double mutations of F3A:W6A served as negative controls. The resulting constructs were transformed to E. coli. XL1 blue and single colonies grown in 1 mL 2YT supplemented with 50 g/mL carbenicillin, 10 μg/mL tetracycline, and M13 KO7 helper phage at 37° C. for 2 h. After the addition of kanamycin (25

µg/mL) and a 6 h incubation at 37° C., the culture was transferred to 30 mL 2YT supplemented with 50 µg/mL carbenicillin and 25 µg/mL kanamycin and grown at 37° C. overnight. Phages were harvested and purified using the standard protocol.

Calibration Curve

The optical fiber was mounted onto a piezo actuator (PAS005, Thorlabs) via a fiber clamp (T711-250, Thorlabs) for precise fiber movement. As shown in FIG. 4a, the total quadrant cell response was calculated by the following:

TABLE 1

M13 Phage samples and descriptions
Displayed Peptide Sequence

| Sample ID | Sample Name | Note | 1 2 3 4 5 6 7 8 9 10 11 12 13 | SEQ ID NO: | Signal Peptide | SEQ ID NO: |
|---|---|---|---|---|---|---|
| 1A, 1B | no SG pep2-8AA-2202 | negative control | T V A T S A E E Y L D W V | 1 | MKIKTGARILALSALTTMMFSASAYA | 6 |
| 2A, 2B | no SG pep2-8-2202 | positive | T V F T S W E E Y L D W V | 2 | MKIKTGARILALSALTTMMFSASAYA | 7 |
| 3A, 3B | no SG pep2-8AA-2478 | negative control | T V A T S A E E Y L D W V | 3 | MKKNIAFLLASMFVFSIATNAYA | 8 |
| 4A, 4B | no SG pep2-8-2478 | positive | T V F T S W E E Y L D W V | 4 | MKKNIAFLLASMFVFSIATNAYA | 9 |
| 5A, 5B | SG pep2-8-2478 | positive | S G T V F T S W E E Y L D W V | 5 | MKKNIAFLLASMFVFSIATNAYA | 10 |

Note: (1) pep2-8 is the ligand that binds to PCSK9; pep2-8AA is the peptide with two critical positions that are involved in binding mutated relative to Ala (SEQ ID NOS: 1 and 3), with no binding to PCSK9; (2) 2202 and 2478, represented phagemids with two different signal peptides, may have different peptide display level on phage; (3) no SG/SG indicating without or with leading sequence of SG before the start of pep2-8 ((SEQ ID NO: 5). This may also affect the peptide display level. (4) Sample groups A and B are identical replicates prepared separately.

Charge-Sensitive Optical Detection Setup

An inverted microscope (Olympus IX-70) with a 40× objective and a quadra-cell position-sensitive photodetector (PDQ80A, Thorlabs) placed at the side camera port were used for CSOD detection. A 96-well microplate with a pair of steel electrodes (1 cm×0.6 cm, 0.8 cm distance) inside the wells were mounted on a motorized microscope stage (Bio-Precision2, Ludl Electronic Products LTD., Hawthorne, NY, USA). Light from a laser (532 nm, 20 mW, Prometheus, Coherent, Santa Clara, CA, USA) was coupled into the fiber via an objective lens (2×, NA 0.06, Olympus). To move the fiber probe between wells, the fiber was clamped to a motorized arm (A-LSQ075B, Zaber, Vancouver, BC, CA) via a post-mounted fiber clamp (T711-250, Thorlabs) to lift the fiber up and down. A sinusoidal potential was applied with a function generator (33521A, Agilent). A USB data acquisition card (USB-6228, National Instruments) was used to record the output of the photodetector.

Surface Functionalization

The tip (about 1 cm) of an optical fiber thread (about 20 cm) was first soaked in acetone for 1 min and then rinsed with DI water and dried. The polymer coating layer on the optical fiber was then stripped off with an optical fiber stripper. The bare fiber was etched by soaking it in 47% hydrofluoric acid for 30 s for a diameter of ~120 µm. The etched fiber was later rinsed with DI water to wash off the hydrofluoric acid and then blow-dried with nitrogen. The tip was cut to about 9 mm long. Before functionalization, the optical fiber was cleaned with oxygen plasma for 3 min.

The etched fiber was soaked in (3-glycidyloxypropyl) trimethoxysilane (epoxy) solution (2.5% volume percentage of epoxy in isopropanol) for 1 h for surface functionalization. The fiber was then rinsed with a PBS buffer. The epoxy modified fiber was soaked in an M13 phage sample solution (10$^7$ pfu/mL in 1×PBS) for 1 h.

$$\text{Response} = \frac{(Q_1 + Q_3) - (Q_2 + Q_4)}{(Q_1 + Q_3) + (Q_2 + Q_4)}, \quad (4)$$

where Q1, Q2, Q3, and Q4 are the responses from each cell. The quadrant cell is equivalent to a bi-cell detector in this configuration. The total quadrant cell response was then plotted against the fiber moving distance provided by the piezo actuator as the calibration curve shown in FIG. 4c.

SPR Measurement

The SPR sensor chip was fabricated by coating 1.5 nm Cr and then 47 nm Au on cover glass (no. 1 VWR) using an e-beam evaporator. Prior to surface functionalization, the gold surface was cleaned with ethanol and DI water twice, dried by N2, and annealed by H2 flame. The gold chip was immersed in a mixture of 0.2 mM SH-PEG8-COOH and 0.2 mM MT(PEG)4 overnight. Then, —COOH was activated using NHS/EDC chemistry (50 mM NHS and 200 mM EDC) for 20 min and incubated with 0.1 mg/mL streptavidin in PBS for 30 min to allow immobilization. The remaining unreacted sites were quenched with 10 mM ethanolamine and the nonspecific binding sites were blocked with Super-Block for 10 min. Next, the streptavidin-coated chip was incubated in 0.5 mM biotinylated pep2-8 for 30 min to capture the peptide on the surface. The functionalized chip was finally rinsed with PBS before the measurement.

Results and Discussion

Proprotein convertase subtilisin/kexin type 9 (PCSK9) regulates plasma low-density lipoprotein (LDL) cholesterol levels by degrading liver LDL receptors. PCSK9 acts by binding to the EGF(A) domain of LDL receptor on the cell surface via its catalytic domain. Previously, a peptide, designated as pep2-8, that inhibits PCSK9 binding to the EGF(A) domain of LDL receptor was reported to be effective in lowering LDL cholesterol. The binding kinetics between PCSK9 protein and phage-displayed pep2-8 in various formats listed in Table 1 were measured using CSOD technology. Pep2-8-displayed M13 phage samples were functionalized to the fiber probe's surface via epoxy coupling. The binding of different concentrations of PCSK9 proteins to the functionalized probes was studied in a 40-time diluted PBS buffer. For each measurement, a baseline was first established by dipping the functionalized fiber tip into a microplate well with a buffer; then, the fiber was switched to another well containing PCSK9 protein solution to measure the association curve. Finally, the fiber was moved back to the buffer well and the dissociation process was recorded. The measured binding kinetics curves are shown in FIG. 5. By fitting the kinetic curves at different concentrations globally with first order kinetics using Scrubber v.2.0c, the association rate constants (ka), dissociation rate constants (kd), and equilibrium constants (KD) for all samples are summarized in Table 2. To confirm the binding specificity, negative controls with mutation of two critical amino acids involved in binding were included. Sample groups 1 and 3 are negative controls with displayed peptides that do not bind to PCSK9 protein. As shown in FIG. 6, PCSK9 has no measurable responses to any negative sample.

Table 2. CSOD measured kinetic and equilibrium constants of PCSK9 binding to phage surface-displayed peptides. The constants were determined by global fitting the sensor response curves at different PCSK9 concentrations relative to first-order

| Sample | Description | $k_a$ (M$^{-1}$·s$^{-1}$) | $k_d$ (s$^{-1}$) | $K_D$ (μM) |
|---|---|---|---|---|
| 2A | no SG pep2-8-2202 | $(1.66 \pm 0.01) \times 10^3$ | $(1.73 \pm 0.03) \times 10^{-3}$ | $1.04 \pm 0.02$ |
| 2B | no SG pep2-8-2202 | $(3.44 \pm 0.01) \times 10^3$ | $(2.91 \pm 0.02) \times 10^{-3}$ | $0.846 \pm 0.008$ |
| 4A | no SG pep2-8-2478 | $(5.05 \pm 0.01) \times 10^3$ | $(2.83 \pm 0.02) \times 10^{-3}$ | $0.560 \pm 0.005$ |
| 4B | no SG pep2-8-2478 | $(3.19 \pm 0.01) \times 10^3$ | $(1.98 \pm 0.03) \times 10^{-3}$ | $0.621 \pm 0.011$ |
| 5A | SG pep2-8-2478 | $(4.20 \pm 0.40) \times 10^3$ | $(1.54 \pm 0.05) \times 10^{-3}$ | $0.370 \pm 0.047$ |
| 5B | SG pep2-8-2478 | $(3.13 \pm 0.01) \times 10^3$ | $(1.19 \pm 0.02) \times 10^{-3}$ | $0.380 \pm 0.008$ |

Figure 7:
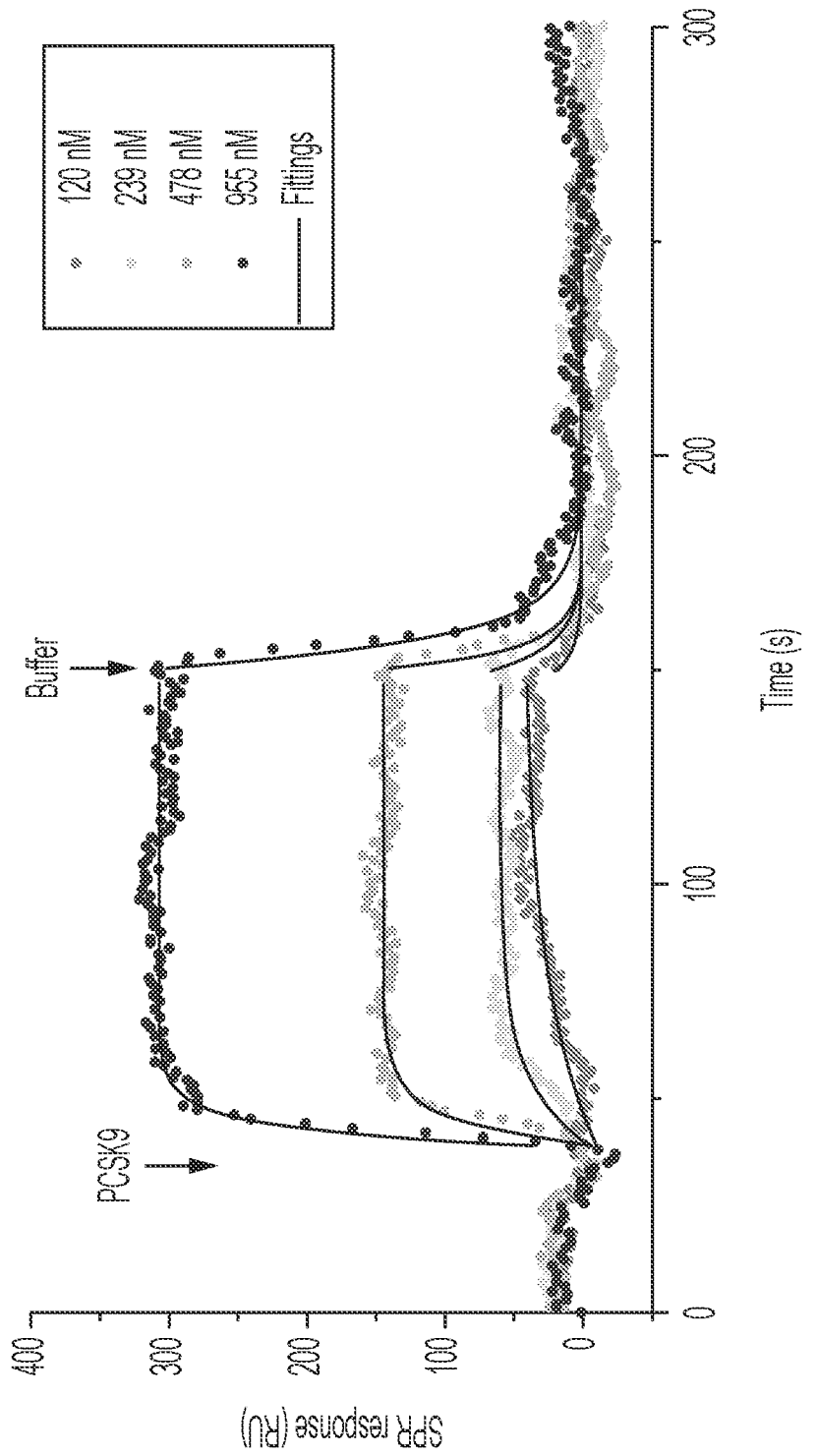
FIG. 7 shows SPR measurement results of PCSK9 binding to synthesized pep2-8. The synthesized peptide was immobilized to a streptavidin-coated gold surface. Different concentrations of PCSK9 were flowed to the surface to measure the binding kinetics. By fitting the data obtained with different concentrations, the average and standard deviation for $k_a$, $k_d$, and $K_D$ were determined to be $(3.88\pm3.26)\times10^5$ $M^{-1}s^{-1}$, $(1.73\pm0.25)\times10^{-1}s^{-1}$, and $0.985\pm0.724$ UM, respectively.

As shown in Table 2, consistent affinity results (20% variation in $K_D$) between sample groups A and B were obtained by CSOD, which are replicates of the same peptide construction, indicating good reproducibility of the method. However, variations in kinetic constants among the different constructed pep2-8 peptide sample group were observed, with twofold affinity variation between phage clones with two different secretion signal peptides (Sample #2 vs. #4), as well as a twofold affinity drop with SG extension (Sample #4 vs. #5) at the N-terminus. These variations in binding constants imply that the peptide's construction methods may affect the binding kinetics of the peptide to the target protein. Nevertheless, the CSOD-measured equilibrium constants KD are in the range of 0.370-1.04 UM among the positive peptide sample groups, which are consistent with the previously reported $K_D$ value of 0.66 UM between synthesized pep2-8 and PCSK9 determined by biolayer interferometry and the IC50 value of 0.81 μM measured by competition ELISA, where the binding of biotinylated PCSK9 to plate-coated LDL receptors is competed off by synthesized pep2-8. To further confirm our results, we performed an additional measurement of synthesized pep2-8—PCSK9 binding using SPR (FIG. 7), which showed that $K_D$ was 0.985±0.724 UM and is also consistent with the above results. Note that the $k_a$ and $k_a$ are different from those determined by CSOD, which implies that the microenvironment of peptides displayed on the phage may have an impact on ligand-binding kinetics.

Unlike reference technologies that can only measure synthesized peptides, CSOD directly measures peptides displayed in very high copy numbers on the phage. Having a high copy number is known to cause the multivalent binding of the target protein and leads to inaccurate binding kinetics, but CSOD can correctly measure the binding kinetics between the peptide and the protein ligand regardless of the copy number of peptides displayed on the phage, because the phage is immobilized on the sensing probe, and the monomer protein ligands are provided in the solution phase. One the other hand, it is impossible for reference technologies to employ the same strategy due to the huge mass of the phage. In addition, CSOD has a wide affinity range from several hundreds of pMs to μM and the detection throughput can be further improved up to 48 binding pairs per microplate.

CONCLUSIONS

We demonstrated the direct quantification of binding kinetics between phage-displayed peptides and the corresponding protein target by CSOD technology. We have shown that CSOD can be used to distinguish different binding kinetics of different peptides displayed by phage display technology. The CSOD-measured dissociation constants were validated by the literature reported values measured with synthetic peptides. These results show that CSOD can be incorporated into a diversity display pipeline for rapidly triaging the best peptide leads during affinity maturation stages and can increase the productivity of library screening.

Some further aspects are defined in the following clauses:

Clause 1: A system for detecting target molecules in a sample. The system comprising a sample well defining a sensing region and two electrode regions, a sensor probe positioned in the sensing region and configured to bind to receptors for target molecules, and an electrode positioned in each electrode region and configured to expose the sensor probe to an alternating electric field, wherein the sensing region defines a channel between the electrodes. The system also includes a light source optically coupled to the sensor probe and configured to provide light along a length of the sensor probe, a position sensitive photodetector configured to detect a position of light exiting the sensor probe, and a processor configured to assess, based at least in part on the position of the light exiting the sensor probe, an amplitude of oscillation of the sensor at a frequency of the alternating electric field and a direction of a displacement of the sensor. The receptors comprise phages or phages displaying peptides, proteins, or antibodies, and the target molecules comprise peptides, proteins, or both.

Clause 2: The system of Clause 1, wherein the sensor probe is an optical fiber.

Clause 3: The system of Clause 1 or Clause 2, wherein a diameter of the optical fiber is in a range of about 100 μm to about 1000 μm.

Clause 4: The system of any one of the preceding Clauses 1-3, wherein a resonance frequency of the optical fiber is in a range of about 100 Hz to about 20 kHz.

Clause 5: The system of any one of the preceding Clauses 1-4, wherein the optical fiber is etched with a strong acid for less than 1 minute.

Clause 6: The system of any one of the preceding Clauses 1-5, wherein the optical fiber is not etched with a strong acid.

Clause 7: The system of any one of the preceding Clauses 1-6, wherein the position sensitive detector is a quadrant cell photodetector.

Clause 8: The system of any one of the preceding Clauses 1-7, wherein a bandwidth of the quadrant cell photodetector is about 150 kHz.

Clause 9: The system of any one of the preceding Clauses 1-8, wherein the frequency of the alternating electric field is in a range of about 5 Hz to about 20 kHz.

Clause 10: The system of any one of the preceding Clauses 1-9, wherein the phages are whole phages.

Clause 11: The system of any one of the preceding Clauses 1-10, wherein the light source comprises a laser, a light emitting diode, or a lamp.

Clause 12: The system of any one of the preceding Clauses 1-11, wherein the receptors and target molecules are label-free.

Clause 13: A system for detecting target molecules in a sample, the system comprising: a sample container comprising two electrode regions and a sensing region disposed between the electrode regions; an optical fiber positioned or positionable in the sensing region, which optical fiber comprises phage-displayed peptide ligands that bind the target molecules in the sample; an electrode positioned or positionable in each electrode region and configured to expose the optical fiber to an alternating electric field; a light source optically coupled to the optical fiber and configured to provide light along a length of the optical fiber; and a position sensitive photodetector configured to detect a position of light exiting the optical fiber.

Clause 14: The system of Clause 13, further comprising a processor operably coupled at least to the position sensitive photodetector, which processor is configured to assess, based at least in part on the position of the light exiting the optical fiber, an amplitude of oscillation of the optical fiber at a frequency of the alternating electric field and a direction of a displacement of the optical fiber.

Clause 15: The system of Clause 13 or Clause 14, wherein the target molecules comprise peptides, proteins, or both.

Clause 16: The system of any one of the preceding Clauses 13-15, wherein the phage-displayed peptide ligands comprise peptides, proteins, or antibodies.

Clause 17: The system of any one of the preceding Clauses 13-16, wherein the phage-displayed peptide ligands and target molecules are label-free.

Clause 18: The system of any one of the preceding Clauses 13-17, wherein a diameter of the optical fiber is in a range of about 100 µm to about 1000 µm.

Clause 19: The system of any one of the preceding Clauses 13-18, wherein a resonance frequency of the optical fiber is in a range of about 100 Hz to about 20 kHz.

Clause 20: The system of any one of the preceding Clauses 13-19, wherein a bandwidth of the position sensitive photodetector is about 150 kHz.

Clause 21: The system of any one of the preceding Clauses 13-20, wherein the frequency of the alternating electric field is in a range of about 5 Hz to about 20 kHz.

Clause 22: The system of any one of the preceding Clauses 13-21, wherein the light source comprises a laser, a light emitting diode, or a lamp.

Clause 23: The system of any one of the preceding Clauses 13-22, wherein the sample container comprises a microplate having a plurality of wells and wherein the optical fiber and the electrodes are positionable in one or more of the plurality of wells such that when the optical fiber and the electrodes are positioned in a given well of the microplate, the given well comprises the electrode and sensing regions.

Clause 24: A method of analyzing a solution to assess the presence target molecules in a sample, the method comprising: providing the sample to a sensing region of a sample well; contacting the sample with a sensor probe comprising molecular receptors configured to interact with the target molecules; providing light along a length of the sensor probe; applying an alternating electric field perpendicular to the length of the sensor probe; detecting a position of light exiting the sensor probe; assessing, based at least in part on the position of light exiting the sensor probe, an amplitude of the oscillation of the sensor probe; and assessing, based at least in part on the amplitude of the oscillation of the sensor probe, the binding kinetics of the target molecules, wherein the molecular receptors comprise phages or phages displaying ligands, and the target molecules comprise peptides, proteins, or both.

Clause 25: The method of Clause 24, wherein the phages comprise whole phages.

Clause 26: The method of Clause 24 or Clause 25, wherein the target molecules are electrically charged.

Clause 27: The method of any one of the preceding Clauses 24-26, further comprising binding the target molecules to the molecular receptors.

Clause 28: The method of any one of the preceding Clauses 24-27, wherein the sensor probe comprises an optical fiber.

Clause 29: The method of any one of the preceding Clauses 24-28, wherein an amplitude of the oscillation of the optical fiber is in a range of 1 nm to 10,000 nm.

Clause 30: The method of any one of the preceding Clauses 24-29, wherein a frequency of the oscillation of the optical fiber is in a range of 5 Hz to 20 kHz.

Clause 31: The method of any one of the preceding Clauses 24-30, wherein the assessing the amplitude of the oscillation of the optical fiber comprises detecting the oscillation with a position sensitive photodetector.

Clause 32: The method of any one of the preceding Clauses 24-31, wherein the position sensitive photodetector is a quadrant cell photodetector.

Clause 33: A method of analyzing a solution to assess the presence target molecules in a sample, the method comprising: contacting the sample with a sensor probe that comprises phage-displayed peptide ligands that bind the target molecules in the sample; applying an alternating electric field perpendicular to the length of the sensor probe; detecting a position of light exiting the sensor probe; assessing, based at least in part on the position of light exiting the sensor probe, an amplitude of the oscillation of the sensor probe; and assessing, based at least in part on the amplitude of the oscillation of the sensor probe, the binding kinetics of the target molecules, thereby analyzing the solution to assess the presence the target molecules in the sample.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A system for detecting target molecules in a sample, the system comprising:
   a sample well defining a sensing region and two electrode regions;
   a sensor probe positioned in the sensing region, which sensor probe comprises receptors for target molecules;
   an electrode positioned in each electrode region and configured to expose the sensor probe to a alternating electric field, wherein the sensing region defines a channel between the electrodes;
   a light source optically coupled to the sensor probe and configured to provide light along a length of the sensor probe;
   a position sensitive photodetector configured to detect and record a position of light exiting the sensor probe using a differential optical position tracking algorithm that calculates sensor probe response, wherein the position sensitive photodetector records only differential and sum signals to reduce data size relative to a charge-coupled device (CCD) camera; and
   a processor configured to assess, based at least in part on the position of the light exiting the sensor probe, an amplitude of oscillation of the sensor at a frequency of the alternating electric field and a direction of a displacement of the sensor,
   wherein the receptors comprise phages or phages displaying peptides, proteins, or antibodies, and the target molecules comprise peptides, proteins, or both.

2. The system of claim 1, wherein the sensor probe is an optical fiber.

3. The system of claim 2, wherein a diameter of the optical fiber is in a range of about 100 μm to about 1000 μm.

4. The system of claim 3, wherein a resonance frequency of the optical fiber is in a range of about 100 Hz to about 20 kHz.

5. The system of claim 3, wherein the optical fiber is etched with a strong acid for less than 1 minute.

6. The system of claim 5, wherein the optical fiber is not etched with a strong acid.

7. The system of claim 1, where the position sensitive detector is a quadrant cell photodetector.

8. The system of claim 7, wherein a bandwidth of the quadrant cell photodetector is about 150 kHz.

9. The system of claim 7, wherein the frequency of the alternating electric field is in a range of about 5 Hz to about 20 kHz.

10. The system of claim 1, wherein the phages are whole phages.

11. The system of claim 1, wherein the light source comprises a laser, a light emitting diode, or a lamp.

12. The system of claim 1, wherein the receptors and target molecules are label-free.

13. A system for detecting target molecules in a sample, the system comprising:
   a sample container comprising two electrode regions and a sensing region disposed between the electrode regions;
   an optical fiber positioned or positionable in the sensing region, which optical fiber comprises phage-displayed peptide ligands that bind the target molecules in the sample;
   an electrode positioned or positionable in each electrode region and configured to expose the optical fiber to an alternating electric field;
   a light source optically coupled to the optical fiber and configured to provide light along a length of the optical fiber; and,
   a position sensitive photodetector configured to detect and record a position of light exiting the optical fiber using a differential optical position tracking algorithm that calculates optical fiber response, wherein the position sensitive photodetector records only differential and sum signals to reduce data size relative to a charge-coupled device (CCD) camera.

14. The system of claim 13, further comprising a processor operably coupled at least to the position sensitive photodetector, which processor is configured to assess, based at least in part on the position of the light exiting the optical fiber, an amplitude of oscillation of the optical fiber at a frequency of the alternating electric field and a direction of a displacement of the optical fiber.

15. The system of claim 13, wherein the target molecules comprise peptides, proteins, or both.

16. The system of claim 13, wherein the phage-displayed peptide ligands comprise peptides, proteins, or antibodies.

17. The system of claim 13, wherein the phage-displayed peptide ligands and target molecules are label-free.

18. The system of claim 13, wherein a diameter of the optical fiber is in a range of about 100 μm to about 1000 μm.

19. The system of claim 13, wherein a resonance frequency of the optical fiber is in a range of about 100 Hz to about 20 kHz.

20. The system of claim 13, wherein a bandwidth of the position sensitive photodetector is about 150 kHz.

21. The system of claim 13, wherein the frequency of the alternating electric field is in a range of about 5 Hz to about 20 kHz.

22. The system of claim 13, wherein the light source comprises a laser, a light emitting diode, or a lamp.

23. The system of claim 13, wherein the sample container comprises a microplate having a plurality of wells and wherein the optical fiber and the electrodes are positionable in one or more of the plurality of wells such that when the optical fiber and the electrodes are positioned in a given well of the microplate, the given well comprises the electrode and sensing regions.

* * * * *